United States Patent [19]

Gries et al.

[11] Patent Number: 5,047,228

[45] Date of Patent: Sep. 10, 1991

[54] NONIONIC 5-C-SUBSTITUTED 2,4,6-TRIIODOISOPHTHALIC ACID DERIVATIVES

[75] Inventors: Heinz Gries; Heinrich Pfeiffer; Ulrich Speck; Wolfgang Mutzel, all of Berlin, Fed. Rep. of Germany

[73] Assignee: Schering Aktiengesellschaft, Berlin and Bergkamen, Fed. Rep. of Germany

[21] Appl. No.: 318,454

[22] Filed: Mar. 2, 1989

Related U.S. Application Data

[63] Continuation of Ser. No. 60,278, Jun. 10, 1987, abandoned, which is a continuation of Ser. No. 855,557, Apr. 25, 1986, abandoned, which is a continuation of Ser. No. 655,669, Sep. 28, 1984, abandoned, which is a continuation of Ser. No. 223,619, Jan. 9, 1981, abandoned.

[30] Foreign Application Priority Data

Jan. 11, 1980 [DE] Fed. Rep. of Germany ....... 3001292

[51] Int. Cl.$^5$ .............................................. A61K 49/04
[52] U.S. Cl. .......................................... 424/5; 560/37; 560/42; 564/153; 564/156
[58] Field of Search ...................... 424/5; 564/153, 156

[56] References Cited

U.S. PATENT DOCUMENTS

| | | | |
|---|---|---|---|
| 4,001,323 | 1/1977 | Felder | 564/153 |
| 4,021,481 | 5/1977 | Almen | 564/153 |
| 4,062,934 | 12/1977 | Tilley | 564/153 |
| 4,250,113 | 2/1981 | Nordal | 560/153 |
| 4,269,819 | 5/1981 | Gries | 424/5 |

Primary Examiner—Michael L. Shippen
Attorney, Agent, or Firm—Millen, White & Zelano

[57] ABSTRACT

Nonionic compounds of the formula

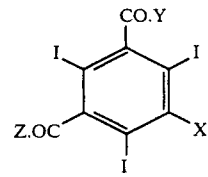

wherein X is $-CONR_1R_2$, $-COOR_3$, $-CH_2NHR_7$ or $-CH_2OH$; Y is $-1R_1R_2$ or $-OR_3$; and Z is $-NR_1R_2$, $-NHR_7$ or $-OR_3$; and wherein $R_1R_2$ and $R_3$ in X, Y or Z, and $R_7$ in X and Z, are identical or different, $R_1$ and $R_2$, and each is hydrogen, $C_{1-6}$-alkyl or $C_{2-8}$- alkyl substituted by 1–5 OH groups and/or by a $C_{1-3}$-alkoxy group; $R_3$ is $C_{1-4}$-alkyl or $C_{2-4}$-alkyl substituted by 1–2 OH groups and/or by a $C_{1-3}$-alkoxy group; and $R_7$ is an acyl group of a $C_{2-5}$ OH group and/or by a $C_{1-3}$-alkoxy group are highly advantageous X-ray contrast agents.

15 Claims, No Drawings

NONIONIC 5-C-SUBSTITUTED 2,4,6-TRIIODOISOPHTHALIC ACID DERIVATIVES

This application is a continuation of application Ser. No. 060,278, filed June 10, 1987, now abandoned, which is a continuation of Ser. No. 855,557, filed Apr. 25, 1986, now abandoned, which is a continuation of Ser. No. 655,669, filed Sept. 28, 1984, now abandoned, which is a continuation of Ser. No. 223,619, filed Jan. 9, 1981, now abandoned.

CROSS REFERENCE TO RELATED APPLICATIONS

This application is related to commonly assigned U.S. Application Ser. No. 223,634, filed Jan. 9, 1981, now U.S. Pat. No. 4,328,202, of common inventorship, whose disclosure is incorporated by reference herein.

BACKGROUND OF THE INVENTION

Since introduction of the triiodinated benzoic acid derivatives as opacifying compounds in X-ray contrast agents for the reproduction of blood vessels, the excretory urinary tract, and other body cavities and tissues, a large number of derivatives has been synthesized, tested, and, in part, also utilized in practice, in ionic contrast media in the form of their salts, as well as in nonionic contrast media.

In this connection, it has been found that the non-physiologically high osmotic pressure of the salt preparations is responsible for a number of incompatibility phenomena, whereby the spectrum of indications of these preparations is limited. This has resulted in the development of nonionic iodine compounds of high water solubility, the osmotic pressure of which is considerably lower.

Metrizamide (U.S. Pat. No. 3,701,771) is regarded as the first well compatible, soluble nonionic opacifying compound suitable for practical radiology. In metrizamide, solubility is obtained by an amide bond of the triiodinated aromatic to glucosamine. In the case of ioglumide (GB 1,436,357), the same is attained by an amide bond of the triiodinated aromatic with gluconic acid. Compounds having such side chains are difficult to prepare, do not show sufficient stability for heat sterilization, and do not have adequate shelf life. This must be considered a grave disadvantage for their practical usage in X-ray contrast media.

Almost all of the aforedescribed nonionic compounds are derived from the two basic structures of triiododiaminobenzoic acid and triiodoaminoisophthalic acid. The existing derivatives of both basic compounds do not satisfy the ever increasing requirements to be met by an ideal X-ray contrast medium. The most important requirements are high contrast density, chemical stability and maximally complete [up to 100%] nontoxicity of the active agent, low viscosity of the liquid preparation, and suitable pharmacodynamic properties adapted to the form of administration. The "ideal contrast medium" should combine all of these requirements. On the other hand, it is known that, due to the requirements regarding contrast density, stability and viscosity, the possibilities of varying the two aforementioned basic structures are considerably restricted, especially also in view of the fact that, for practical usage, compounds having a high iodine content are generally considered. Since the possibilities of synthesizing such compounds have been extensively exhausted in the meantime, the introduction of a novel basic structure is of special value.

The relatively good compatibility of the X-ray contrast media used nowadays is attained by detoxifying the actually lipophilic and toxic basic compounds [i.e. structures] by strongly hydrophilic substituents.

SUMMARY OF THE INVENTION

Accordingly, it is an object of the present invention to provide such novel basic structures which even by themselves are maximally hydrophilic and nontoxic, and from which may be prepared novel and improved contrast media.

Upon further study of the specification and appended claims, further objects and advantages of this invention will become apparent to those skilled in the art.

These objects have been attained by providing novel, nonionic 2,4,6-triiodoisophthalic acid derivatives which are C-substituted in the 5-position and are of Formula

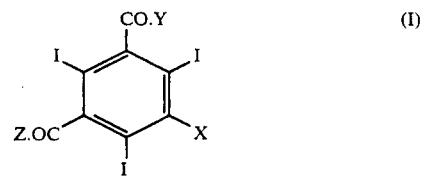

wherein
X is —$CONR_1R_2$, —$COOR_3$, —$CH_2NHR_7$ or —$CH_2OH$,
Y is —$NR_1R_2$ or —$OR_3$,
Z is —$NR_1R_2$, —$NHR_7$ or ——$OR_3$,
wherein $R_1R_2$ and $R_3$ in X, Y, and Z, and $R_7$ in X and Z, can be identical or different,
$R_1$ and $R_2$, can be identical or different, and each is hydrogen or an optionally mono- or polyhydroxylated, straight-chain or branched alkyl, wherein any OH-groups present can also be etherified,
$R_3$/lower, optionally hydroxylated alkyl, wherein any OH-groups present can also be etherified, and
$R_7$ is the acyl residue of an optionally hydroxylated, lower aliphatic carboxylic acid, wherein any OH-groups present can also be etherified.

The present invention also relates to a process for the preparation of these compounds and to novel X-ray contrast media containing them as the opacifying substance.

DETAILED DISCUSSION

The unsubstituted alkyl groups $R_1$ and $R_2$, which can be straight-chain or branched, contain 1-6, preferably 1-4, and particularly 1-2 carbon atoms. Examples include, in particular, methyl, ethyl and propyl. Methyl is preferred.

If the alkyl group is a mono- or polyhydroxyalkyl residue, it also can be straight-chain or branched. Preferably suitable are alkyl residues of 2-8, preferably 2-4 carbon atoms. The hydroxy groups in the alkyl residue can be present as primary and/or secondary and/or tertiary hydroxy groups. The alkyl group can contain 1-5, preferably 1-3 hydroxy groups. Examples include tris(hydroxymethyl) methyl, hydroxyethyl, especially 1,3- and 2,3- dihydroxypropyl, and 2,3-dihydroxy-1-hydroxymethylpropyl.

$R_3$ is lower alkyl of 1-4, preferably 1-2 carbon atoms. Methyl is preferred. If $R_3$ is hydroxylated, it contains preferably 2-4 carbon atoms in the alkyl residue and can carry 1-2 hydroxy groups, preferably one hydroxy group. Examples of hydroxylated alkyl residues $R_3$ include dihydroxypropyl and, preferably, hydroxyethyl.

When the substituent Z and/or X is or contains the residue $—NHR_7$, the acyl residue $R_7$ is derived from an aliphatic carboxylic acid of 2-5 carbon atoms. Suitable ones, in particular, include aliphatic carboxylic acid residues of 2-4 carbon atoms, e.g., propionyl and, preferably, acetyl.

Preferably suitable are acyl residues $R_7$ substituted in the alkyl portion by 1-4, preferably 1-3 hydroxy groups. Examples include hydroxyacetyl, 2-hydroxypropionyl, and 2,3-dihydroxypropionyl.

Any OH-Group present in the alkyl groups $R_1$, $R_2$, $R_3$, $R_4$, $R_5$ and in the acyl group $R_7$ can be etherified with a lower alkyl group of 1-3, preferably 1-2 carbon atoms, examples include methoxy and ethoxy.

The present invention comprises nonionic X-ray contrast media based on the opacifying compounds of this invention with novel basic structures. These novel opacifying compounds are distinguished by a number of advantages. They are derived from triiodinated aromatic basic components which themselves are hydrophilic and nontoxic. The heretofore conventional introduction of very voluminous hydrophilic substituents to lessen chemotoxicity has thus become dispensable, whereby the compounds of this invention possess a desirably high iodine content. They are also distinguished by a high chemical stability, especially also under the conditions of heat sterilization.

Solutions of the compounds of this invention can thus also be sterilized in the usual way by heating to 120° C. at a physiological pH value. The solutions have a low osmotic pressure even at high iodine concentrations, compared with the state of the art ionic X-ray contrast media. This is especially a prerequisite for a good local compatibility.

The compounds of this invention exhibit, in various conventional tests on different animal species, a very high general compatibility and an excellent local compatibility, a very good cardiovascular compatibility, and only low neurotoxicity. Moreover, the compounds of this invention show in the in vitro test only an extremely minor interaction with proteins and only a very minor membranedamaging effect. Furthermore, the novel compounds show only a low epileptogenic activity upon subarachnoid administration.

The highly water-soluble compounds are suitable for all uses where iodine-containing, renally excretory contrast media are applicable, such as, for example, angiography, urography, computer tomography, gastrointestinal visualization, arthrography, and myelography. The compounds of this invention are preferably employed in the fields of angiography, myelography, and in those indications wherein the X-ray contrast medium is not very quickly diluted, in contrast with those wherein intravenous administration is indicated, so that local compatibility plays a significant role.

The compounds of this invention exhibiting sparing water solubility are likewise highly compatible, because they have, in spite of their low water solubility, an extraordinary hydrophilic character. In any event, their local compatibility is markedly better than that of the esters of ionic contrast media heretofore employed experimentally and clinically. These include the ethyl ester of iothalamic acid, of iodipamide, and of iopodic acid.

The field of application of these compounds encompasses all possibilities described in the literature for utilization of particle-containing contrast media, such as angiography, computer tomography, direct and indirect lymphography, gastrointestinal visualization, bronchography and the visualization of other body cavities. Preferred in such cases is the use of the compounds in the form of powders or microcrystalline suspensions, optionally containing suitable stabilizers, such as gelatin, human albumin, dextran, polyvinylpyrrolidone, and similar materials. The thus-administered, sparingly water-soluble novel contrast media are gradually dissolved by the organism and are excreted predominantly renally.

The following table contains a comparison of several of the above-mentioned advantageous properties of the novel nonionic X-ray contrast media of this invention using the conventional metrizamide (A) and the following opacifying compounds: 2,4,6-triiodobenzene-1,3,5-tricarboxylic acid tris(2,3-dihydroxypropyl-N-methyl)-triamide (B); 2,4,6-triiodobenzene-1,3,5-tricarboxylic acid tris(bis-2-hydroxyethyl)triamide (C); 2,4,6-triiodobenzene-1,3,5-tricarboxylic acid bis(2,3-dihydroxypropyl-N-methyl)triamide (D); 2,4,6-triiodobenzene-1,3,5-tricarboxylic acid tris(2,3,4,5,6-pentahydroxyhexyl-N-methyl)triamide (E); 2,4,6-triiodobenzene-1,3,5-tricarboxylic acid [(N,N-dimethyl)-bis(2,3-dihydroxypropyl)]-triamide (F); and 5-N-methylcarbamoyl-2,4,6-triiodoisophthalic acid bis(2,3-dihydroxy-1-hydroxymethylpropyl)diamide (G).

TABLE 1

| | Properties of Novel Nonionic X-Ray Contrast Media as Compared with Metrizamide | | | | | |
|---|---|---|---|---|---|---|
| Compound | Iodine Content | Stable in Heat Sterilization | Distribution Coefficient Butanol/Buffer pH 7.6 | Erythrocyte Damage | $LD_{50}$ Mouse (i.v.)* (g Iodine/kg) | $LD_{50}$ Rat (i.v.)* (g Iodine/kg) |
| A | 48 | No | 0.259 | 10 | 12 | 11 |
| B | 45 | Yes | 0.064 | 2.1 | 16 | 11 |
| C | 45 | Yes | 0.131 | 1.8 | | 12 |
| D | 50 | Yes | 0.074 | 4.2 | | |
| E | 34 | Yes | <0.001 | <0.3 | | |
| F | 50 | Yes | 0.171 | 2.7 | 14 | 11 |
| G | 47 | Yes | 0.065 | 2.8 | | 19 |

*Injection rate 2 ml/min; concentration 300 mg/ml; observation period 24 h.

The distribution coefficient of a compound permits ascertainment of its hydrophilicity and thus its compatibility; the lower the value of the distribution coefficient, the higher the compatibility of the compound tested.

The deformation of erythrocytes (erythrocyte damage) due to X-ray contrast media can be taken as a measure for the membrane-damaging effect of the compound. In this instance, the formation of echinocytes was measured in dog erythrocytes, setting the effect of metrizamide at 10 as a standard. A smaller number signifies a correspondingly higher compatibility.

The present invention also concerns novel X-ray contrast media comprising as opacifying agent, a compound of Formula I, for administration to mammals, including humans.

The novel X-ray contrast media based on the compounds of this invention are prepared in a manner known per se, for example by bringing the opacifying compound into a form suitable for the desired administration e.g., intravenously, rectally, orally, etc. with the additives suitable in galenic pharmacy, for example stabilizers such as sodium edetate, calcium disodium edetate, physiologically compatible buffers; sodium chloride, and similar compounds. The concentration of the novel X-ray contrast media in an aqueous medium is entirely dependent on the method used for X-ray diagnostics and is fully conventionally determinable using well known methods based on any of the well known dosage determination techniques, e.g., in comparison with dosages for known contrast media. The preferred concentrations and dosages of the novel compounds range from 50 to 400 mg I/ml and 5–500 ml per dose, respectively. Especially preferred are concentrations of 100 to 400 mg I/ml. Methods of administration are analogous to those conventionally employed with known agents such as metrizamide.

The present invention furthermore relates to a process for preparing compounds of Formula I, comprising conventionally, (a) reacting a compound of general Formula II

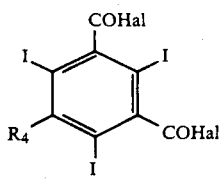
(II)

wherein
Hal is a halogen atom, preferably a Cl atom and
$R_4$ is the group —COHal,

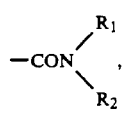

—CONHR$_7$, —CH$_2$NHR$_7$, or —CH$_2$OH (wherein Hal, $R_1$, $R_2$ and $R_7$ are as defined above)
with a base of Formula IIIA

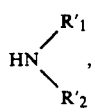
(IIIA)

(wherein $R'_1$ and $R'_2$ have the same meanings as $R_1$ and $R_2$ but are not both hydrogen simultaneously),
or, in stages, reacting the 1-positioned —COHal-group with the base IIIA and reacting the 3-positioned —COHal-group with a base IIIB of the formula

(IIIB)

(wherein $R''_1$ and $R''_2$ have the same meaning as $R_1$ and $R_2$ but are not both hydrogen simultaneously and are different from $R'_1$ and/or $R'_2$); or (b) reacting a compound of Formula IV

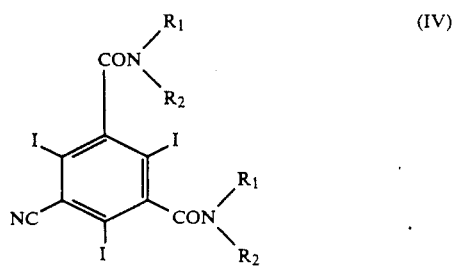
(IV)

wherein $R_1$ and $R_2$ are as defined above, with the reactive derivative of an aliphatic carboxylic acid $R_7$—OH, or treating it with an alkali in an aqueous solution, and subsequently diazotizing the thus-obtained 5-carbamoyl compound if desired, in an aqueous solution and in the presence of a strong acid, and amidating the thus-formed 5-carboxy group with a 2-amino sugar or with the base HNR'$_1$R'$_2$ (R'$_1$ and R'$_2$ being as defined above) or esterifying it with an alcohol R$_3$OH; or (c) esterifying a compound of Formula V

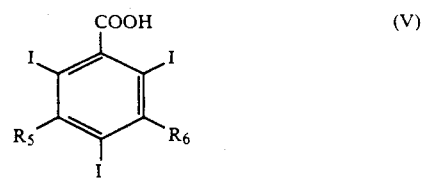
(V)

wherein
$R_5$ is —CH$_2$OH,

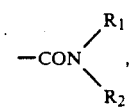

—CH$_2$NHR$_7$, or —COOH, and
$R_6$ is

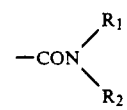

or —COOH, with an alcohol R$_3$OH (R$_3$ being as defined above, and, optionally, subsequently, acylating hydrogen-containing amino groups with a reactive derivative of an aliphatic carboxylic acid R$_7$—OH (R$_7$ being as defined above) and/or N-alkylating them with an R'$_1$-containing alkylating agent, and/or liberating blocked hydroxy groups.

The amidation reactions used during the course of the process for preparing the compounds of Formula I are performed by following conventional methods.

The residue Hal in the starting compound of Formula II is a halogen atom, e.g., iodine, bromine, or especially chlorine.

For the amidation reaction, hydroxy groups present in the substituents $R'_1$, $R'_2$, $R''_1$, and $R''_2$ can be in the free or blocked form. When these hydroxy groups are present in the blocked form, all customary hydroxy blocking groups can be used, which are conventionally suitable for intermediate hydroxy group protection, i.e., groups which can be readily introduced and also easily split off subsequently under reformation of the finally desired, free hydroxy group. Protection by means of acylation is preferred, especially by acetylation or by acetalization with, for example, acetaldehyde, or by ketalization with, for example, acetone or 2,2-dimethoxypropane. Suitable blocking groups also include ether groups, such as, for example, benzyl, di-and triphenylmethyl ether groups.

The amidation of the two 1- and 3-positioned COHal-groups can be effected in one reaction step or also in stages. If the two 1- and 3-positioned amide residues in the finally desired product of the process are identical with respect to the N-substituents $R_1$ and $R_2$, then the amidation takes place preferably in one reaction step. However, if these two amide groups differ with respect to the N-substituents $R_1$ and $R_2$ then the amidation is preferably effected in stages.

The two amidation reactions can be effected in a suitable solvent at 0–100° C., preferably at 20–80° C. Suitable solvents are, inter alia, polar solvents. Examples include water, dioxane, tetrahydrofuran, dimethylformamide, dimethylacetamide, hempa, and similar compounds and mixtures thereof. Since the amidation reaction takes place exothermally, it is sometimes advantageous to cool the reaction mixture. Hydrogen halide, for example hydrogen chloride, is liberated during the amidation reaction and must be bound for neutralizing purposes. For this reason two equivalents of the base are required per acid chloride group, suitably with an excess of base of about 10%.

For the preparation of final products wherein the amide groups to be introduced are identical, the dissolved starting compound II is reacted with 4 equivalents of the base IIIA or with 2 equivalents of the base IIIA in the presence of 2 equivalents of a preferably tertiary base which then serves as the proton acceptor.

For preparing final products wherein the amide groups to be introduced are different, the dissolved starting compound is first reacted with 2 equivalents of the base IIIA or with one equivalent of the base IIIA in the presence of a preferably tertiary base.

The monoamide is suitably isolated in conventional manner to avoid secondary reactions during further processing and reacted with the base IIIB in a second stage to form the diamide in an analogous fashion.

If the first amidation stage with base IIIA takes place in the presence of a preferably tertiary base, the second amidation stage with base IIIB can optionally also be conducted without isolation of the initially formed monoamide in a single-reactor (one-pot) procedure.

If, in the starting compound of Formula II, the substituent $R_4$ is also a —COHal-group, then amidation with 6 equivalents of base IIIA or with 3 equivalents of base IIIA in the presence of 3 equivalents of a preferably tertiary base, yields the corresponding 1,3,5-tris amide of 2,4,6-triiodotrimesic acid wherein the three amide groups are identical.

Also, in this case, it is possible to effect the amidation of the three carboxy groups in a stepwise fashion. If in the first stage the amidation is carried out with a base IIIA, in the second stage with a base IIIB, and in the third stage with a base $HNR'''_1R'''_2$ (IIIC; $R'''_1$ and $R'''_2$ having the same meaning as $R_1$ and $R_2$ but are not simultaneously hydrogen and being different from $R'_1$, $R'_2$, $R''_1$, and $R''_2$), then it is also possible to produce 1,3,5-tris amides of Formula I wherein the three amide groups are differently N-substituted with respect to $R_1$ and $R_2$.

Tertiary bases, such as, for example, triethylamine, tributylamine, or pyridine are advantageously employed for binding the hydrogen chloride formed during amidation. However, inorganic proton acceptors can also be used, such as calcium carbonate, for example.

The organic salts obtained during the course of the reaction are conventionally separated, advantageously, for example, using conventional ion exchangers, such as, e.g., "Amberlite JR 120", or columns, or by filtration over conventional adsorber resins, e.g., "Amberlite XAD-2" and "Amberlite XAD-4".

If the course of reaction makes it necessary to intermediately block any free hydroxy groups present in the substituents $R_1$ and/or $R_2$ and/or $R_3$ and/or $R_7$, this is accomplished according to conventional methods by means of readily cleavable groups. The introduction of such blocking groups can take place, for example, by acylation (e.g., introduction of preferably an acetyl residue or benzoyl residue) or by etherification (e.g., introduction of the triphenylmethyl residue).

The hydroxy groups can also be blocked by ketalization or acetalization, e.g., by means of acetaldehyde, acetone, or dihydropyran.

The subsequent splitting off of the intermediately introduced blocking groups with liberation of the finally desired hydroxy groups is likewise accomplished according to methods generally known to those skilled in the art. Thus, the blocking groups can be split off without a separate reaction stage during the working up and isolation of the reaction products. However, it is also possible to conduct this procedure in a separate reaction stage. Acyl blocking groups can be split off, for example, by alkaline hydrolysis, and acetal, ketal, or ether blocking groups can be cleaved by acidic hydrolysis.

The conversion of the cyano group into the N-acylated amido group —$CONHR_7$ occurs by chemical addition of an aliphatic carboxylic acid $R_7COOH$ to the CN-triple bond according to methods known to persons skilled in the art. In practice, the acid $R_7COOH$ is suitably employed in the form of a reactive derivative, preferably as the anhydride. The reaction takes place in the presence of a suitable acidic catalyst, such as, for example, perchloric acid or sulfuric acid, phosphoric acid, and similar compounds. The acid anhydride employed normally also simultaneously serves as the solvent. This does not exclude the possibility of adding a suitable solubilizer, such as dioxane, to the reaction mixture. The reaction is conducted at room temperature or elevated temperature. If the reaction takes place at an elevated temperature, the preferred temperature range is 40–110° C.

The conversion of the cyano group in the starting compound of Formula IV into the carbamoyl group likewise takes place according to methods with which persons skilled in the art are fully familiar. Suitably, the starting compound is hydrolyzed in water in the presence of excess alkali at room temperature or elevated temperature, for example at 0–80° C. Potassium or sodium hydroxide is especially used as the alkali; this compound can be added to the reaction mixture in the solid phase or, for example, as a 2N alkali hydroxide solution. Optionally, the aqueous reaction mixture can also be combined with an organic solubilizer, e.g. methanol, dioxane, tetrahydrofuran, or similar organic solvents.

The partial saponification of the cyano group to the carbamoyl group can also be conducted in the acidic pH range, for example in concentrated sulfuric acid at an elevated temperature, for example 50–90° C.

The optionally following diazotization of the carbamoyl group to the carboxy group takes place conventionally using reagents customary for this purpose, e.g. nitrosyl chloride, nitrosylsulfuric acid, or sodium or potassium nitrite, in the presence of an acid such as, for example, hydrochloric acid, sulfuric acid, and others. In the practical conductance of the process, the compound to be diazotized is suspended, for example, in a mixture of water/concentrated hydrochloric acid and gradually combined with an aqueous sodium nitrite solution. The reaction takes place at room temperature or suitably at an elevated temperature, preferably at 40–100° C.

The diazotization can also be conducted just as advantageously by reacting the carbamoyl compound in an organic solvent such as acetic acid or dimethylformamide, for example, with nitrosyl chloride or with nitrosylsulfuric acid.

If the free carboxy group is to be converted per this invention into the amide group $-NR_1R_2$ or $-NH$-Sugar residue, the amidation takes place as usual; for example, by first converting the carboxy group, optionally in the presence of a suitable solvent, e.g., dimethylformamide, toluene, acetonitrile, and similar solvents, using, for example, thionyl chloride, phosphorus pentachloride, phosgene, or 1,1-dichloromethylmethyl ether, into the acid chloride group and then reacting the latter as explained in greater detail above with $HNR'_1R_2$ (IIIA) or with an amino sugar.

Especially suitable as the amino sugars, wherein the amino group is preferably bound in the 2-position, are those of 4–6 carbon atoms in the sugar residue. Preferably suitable is 2-aminoglucose.

If the carboxy group is to be present in the final compound as an ester group $-COOR_3$, then the esterification of the free carboxy groups also takes place according to methods known per se. If the ester residue $-COOR_3$ contains hydroxy groups in the alkyl residue, such an ester residue is suitably introduced by reacting the alkali salt of the acid, preferably the sodium salt, in a suitable solvent, preferably dimethylformamide or also dimethylacetamide, with the corresponding alkyl halogenide, preferably chloride.

Besides this esterification method, which is preferred within the scope of the present invention, the esterification of the free carboxy groups can also be accomplished by the following other customary methods, especially when the $R_3O$ residue to be introduced does not contain any additional hydroxy groups in the alkyl residue $R_3$. One example is the esterification with corresponding diazoalkanes, e.g., diazomethane, diazoethane, or the reaction of the free carboxy group with an alcohol $R_3OH$, preferably in the presence of, for example, a mineral acid such as sulfuric acid.

The compounds of this invention can contain 1–3 esterified carboxy groups; when there is more than one ester group in the molecule, the ester residues $-COOR_3$ can be identical or different.

The esterification of free carboxy groups in the starting compound IV or V also can be effected according to methods generally known to those skilled in the art. One example of a preferred esterification method is the reaction of the carboxy group in the form of the alkali salt with an $R_3$-halogenide, as explained in greater detail hereinabove.

For producing compounds of Formula I which contain only one $-COOR_3$-group, compounds of Formula IV can be suitably employed as the starting materials; and the 5-positioned cyano group is converted into the finally desired ester group $-COOR_3$ in accordance with process version (b).

If the finally desired compounds of Formula I are to contain two or also three $-COOR_3$-groups, they are produced suitably by following process version (c), wherein the residue $R_5$ and/or $R_6$ in the starting compound of Formula V represents $-COOH$.

If the thus-obtained compounds according to this invention contain primary and/or secondary amide groups, these can be additionally N-alkylated and/or acylated, if desired, according to various methods known to those skilled in the art, optionally after an intermediate protection of free hydroxy groups.

The subsequent N-alkylation is conducted, for example, by treating the corresponding acid amide first of all with a proton acceptor, such as sodium amide, sodium hydride, or also an alkali hydroxide, and then reacting the same with an $R_1$- or $R'_1$-alkyl halogenide, preferably as the bromide, or especially with a di-$R_1$(or $R'_1$)sulfate (e.g., dimethyl or diethyl sulfate). Depending on the proton acceptor employed, the reaction takes place in an anhydrous or aqueous reaction medium at a reaction temperature of about room temperature to 100° C., preferably 50–70° C.

Suitable solvents, or solubilizers include, as is known, acetone, dimethylformamide, dioxane, tetrahydrofuran, and similar compounds.

If the initially obtained compounds of this invention as represented by Formula I are to be acylated as is optional, then the acylation of the amide groups which still contain hydrogen is likewise effected according to known processes, for example by reacting the amide in an inert solvent, e.g., pyridine, DMA, DMF, and similar compounds, at temperatures of 0° C. to room temperature, with a reactive acid derivative, preferably the corresponding acid halogenide, especially the acid chloride, or also with a corresponding acid anhydride, preferably in the presence of an acidic catalyst, such as, for example $H_2SO_4$.

The starting compounds used in these processes can be prepared by conventional methods, for example from the known compounds of the formula

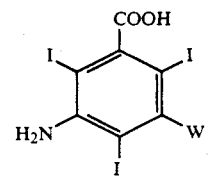

wherein W is —COOH, —CH$_2$NHR$_7$, or —CH$_2$OH, by proceeding in such a way that, in any desired sequence, the 5-positioned amino group is substituted by the cyano group with the aid of the Sandmeyer reaction, and the substituents —COOH, W, and CN are converted, according to methods known to a skilled chemist conducting experimental work in the art, into the finally desired residues of the preliminary products and/or starting compounds used according to this invention, as will be explained in detail by the following exemplary description.

The substitution of the aromatic amino group by the cyano group will be explained, by using as an example the preparation of 5-cyano-2,4,6-triiodoisophthalic acid in greater detail:

112 g of 5-amino-2,4,6-triiodoisophthalic acid is suspended in 1100 ml of water and dissolved by adding 10 g of sodium hydroxide. The solution is then cooled to 0° C. after adjusting same to pH 2.5 with sulfuric acid, and, under cooling, a solution of 20 g of sodium nitrite in 60 ml of water is added dropwise, the reaction temperature being maintained at 0-5° C. Then the pH value of the reaction mixture is again adjusted to 2.5 by the dropwise addition of dilute sulfuric acid, and the mixture is stirred under ice cooling for one to two hours. The thus-obtained precipitate is dissolved by gradual dropwise addition of dilute sodium hydroxide solution at pH 4.5. Subsequently the neutralized diazonium salt solution is poured into a solution of 99 g of copper(I) chloride and 172 g of potassium cyanide in 800 ml of water, heated to 30° C.; during this step, strong frothing occurs. The mixture is stirred for 15 minutes at 30° C. The reaction mixture is then acidified with dilute sulfuric acid to pH 2.8-3, and the precipitated copper salt is vacuum-filtered. The filtered solution is then brought to pH 0.5-1 by the further addition of dilute sulfuric acid. The thus-produced precipitate is vacuum-filtered after stirring for several hours in an ice bath, washed with water, and dried at 50° C. For purifying purposes, the crude product is suspended in 400 ml of water, dissolved by adding sodium hydroxide solution, the solution treated for 30 minutes with 10 g of active carbon, and the filtered solution is combined with an excess of a mineral acid. After stirring for several hours in an ice bath, the precipitate is vacuum-filtered, washed with water, and dried at 50° C., thus obtaining 89 g (78% of theory) of 5-cyano-2,4,6-triiodoisophthalic acid as a white powder, having a decomposition point of above 300° C.

Analogously, the following compounds are produced from the corresponding 5-amino compounds:

5-cyano-2,4,6-triiodoisophthalic acid monomethylamide, mp above 300° C. (decomposition); yield 72% of theory;

5-cyano-2,4,6-triiodoisophthalic acid bis(2-hydroxyethyl)amide, mp above 300° C. (decomposition); yield 68 of theory;

5-cyano-2,4,6-triiodoisophthalic acid mon-N-(2-hydroxyethyl)amide, mp above 300° C. (decomposition); yield 95% of theory;

5-cyano- 3-acetylaminomethyl-2,4,6-triiodobenzoic acid, mp 271° C. (decomposition); yield 85% of theory;

5-cyano-2,4,6-triiodoisophthalic acid monodimethylamide, mp 240° C. (decomposition); yield 85% of theory;

5-cyano-N-(2-hydroxyethyl)-N-methyl-2,4,6-triiodoisophthalamic acid, mp above 280° C. (decomposition); yield 89% of theory;

5-cyano-3-hydroxymethyl-2,4,6-triiodobenzoic acid, mp 250-252° C. (decomposition); yield 81% of theory;

5-cyano-2,4,6-triiodoisophthalic acid monoamide, mp above 300° C. (decomposition); yield 82% of theory.

Suitably, 5-cyano starting compounds are utilized for preparing the starting material of general Formula II [process version (a)].

Depending on the finally desired significance of the 5-positioned substituent (in compound II=R$_4$), the cyano group is first conventionally saponified in an acidic or alkaline process, thus obtaining the corresponding amide. This saponification reaction will be explained in greater detail, using 5-cyano-2,4,6-triiodoisophthalic acid as an example:

100 g of 5-cyano-2,4,6-triiodoisophthalic acid is suspended in 400 ml of water and dissolved by adding 20 g of sodium hydroxide. The solution is maintained at +60° C. for 3 hours, then poured under agitation into 60 ml of concentrated hydrochloric acid. After several hours of stirring in an ice bath, the precipitate is vacuum-filtered, washed with a small amount of ice-cooled water, and dried at 50° C., thus obtaining 98 g (=95% of theory) or 5-carbamoyl-2,4,6-triiodoisophthalic acid having a decomposition point of above 280° C., as a white powder.

Analogously, the following corresponding initial or starting compounds are prepared:

5-carbamoyl-N-(2-hydroxyethyl)-2,4,6-triiodoisophthalamic acid, mp 310–312° C. (decomposition); yield 49.7% of theory;

5-carbamoyl-2,4,6-triiodoisophthalic acid monodimethylamide, mp 255° C.; yield 85% of theory;

5-carbamoyl-N-(2-hydroxyethyl)-N-methyl-2,4,6-triiodoisophthalamic acid, mp 286–288° C.; yield 55.9% of theory;

5-carbamoyl-2,4,6-triiodoisophthalic acid monomethylmonoamide, purified by way of the dimethylamine salt, mp >300° C.; yield 76.5% of theory;

5-hydroxymethyl-2,4,6-triiodoisophthalamic acid, mp above 300° C. (decomposition); yield 78% of theory;

5-acetylaminomethyl-2,4,6-triiodiisophthalamic acid, mp 220–222° C.; yield 75% of theory;

5-carbamoyl-2,4,6-triiodoisophthalic acid bis(2-hydroxyethyl)diamide, mp above 300° C. (decomposition); yield 75% of theory;

5-carbamoyl-2,4,6-triiodoisophthalic acid mono-(2,3-dihydroxy-propyl)mono-(2,3-dihydroxypropyl-N-methyl)diamide, mp 202° C.; yield 61% of theory.

The thus-obtained 5-carbamoyl group can be converted into the carboxy group in the usual way, suitably in an aqueous-acidic solution by means of a diazotizing reagent, e.g. sodium nitrite, as indicated above, and as will be explained once more in greater detail, using 2,4,6-triiodotrimesic acid as an example:

100 g of 5-carbamoyl-2,4,6-triiodoisophthalic acid is suspended in 2 l of semiconcentrated hydrochloric acid, and the suspension is heated to 90° C. under agitation. Within 5 hours, a solution of 59 g of sodium nitrite in 1 l of water is introduced underneath the surface level of this solution; then the solution is stirred for another 2 hours at 90° C. Subsequently the solution is concentrated to dryness under vacuum, and the residue is extracted for 1 hour with 1 l of ether. The product is vacuum-filtered from the precipitated sodium chloride and, after evaporation of the ether solution, 98 g of 2,4,6-triiodo-1,3,5-tricarboxylic acid is obtained as a white powder having a decomposition point lying above 80° C.; yield 99% of theory.

Analogously, the following compounds are produced from the corresponding 5-carbamoyl compound:

2,4,6-triiodobenzene-1,3,5-tricarboxylic acid monomethylmonoamide, mp >300° C.; yield 99% of theory;

2,4,6-triiodo-1,3,5-tricarboxylic acid (2-hydroxyethyl)-monoamide, mp above 300° C.; yield 63% of theory;

5-(N,N-dimethylcarbamoyl)-2,4,6-triiodoisophthalic acid, mp above 300° C. (decomposition); yield 72% of theory;

2,4,6-triiodobenzene-1,3,5-tricarboxylic acid monomethylamide, mp above 300° C. (decomposition); yield 79% of theory.

For the amidation reactions conducted according to this invention, initial products or starting compounds are suitably those wherein the carboxy group to be amidated is present as the acid halogenide, for example the acid chloride. The conversion of the carboxy group into the acid halogenide group takes place according to methods known in general to those skilled in the art, as will be demonstrated, using as an example 2,4,6-triiodotrimesic acid trichloride preparation:

147 g of 2,4,6-triiodotrimesic acid, 588 ml of thionyl chloride, and 1.3 ml of dimethylformamide are stirred for 2 hours under reflux on a steam bath, causing at the beginning a vigorous HCl liberation. The solution is then concentrated under vacuum at about +50° C., and the residue is agitated for 2 hours with 1.5 l of toluene. A small amount of undissolved compound is removed by vacuum-filtering and discarded. The filtrate is concentrated under vacuum at about +50° C., and the residue is dried at +60° C. under vacuum; yield: 151 g (93.9% of theory), mp 258–260° C.

Analogously, the following compounds are obtained, for example, from the corresponding acids:

5-cyano-2,4,6-triiodoisophthalic acid dichloride, mp 278–280° C. (from toluene); yield 90% of theory;

5-carbamoyl-2,4,6-triiodoisophthalic acid dichloride, mp 247–248° C. (decomposition); yield 58.7% of theory;

5-N-methylcarbamoyl-2,4,6-triiodoisophthalic acid dichloride, mp 214–216° C.; yield 97.9% of theory;

5-N,N-dimethylcarbamoyl-2,4,6-triiodoisophthalic acid dichloride, mp 272–273° C.; yield 85% of theory;

2,4,6-triiodobenzene-1,3,5-tricarboxylic acid dichloride mono-(2-hydroxyethyl)amide, mp 75–85° C.; yield 93% of theory;

2,4,6-triiodobenzene-1,3,5-tricarboxylic acid monochloride bis(2-acetoxyethyl)diamide, mp 202–204° C.; yield 75% of theory;

2,4,6-triiodo-3,5-bis(N-methylcarbamoyl)benzoic acid chloride, mp 293–295° C. (decomposition); yield 96% of theory.

It is also possible according to the process of this invention to begin with initial or starting compounds wherein the finally desired amide residue —NR$_1$R$_2$ is already contained. The introduction of this amide residue into suitable precursors then takes place according to methods with which the expert is generally familiar and preferably according to methods as dealt with above, especially in connection with the explanations of process version (a). In this connection, the introduction of the amide residue will once more be illustrated, using as an example the preparation of 5-cyano-2,4,6-triiodoisophthalic acid bis(2,3-dihydroxypropyl-N-methyl)diamide from the dichloride 100 g of 5-cyano-2,4,6-triiodoisophthalic acid dichloride is dissolved at 50° C. in 200 ml of dimethylacetamide. A solution of 42.8 g of 1-N-methylamino-2,3-propanediol in 120 ml of dimethylacetamide is added dropwise to this reaction mixture within 10 minutes. After the addition of 97 ml of n-tributylamine, the reaction mixture is stirred for 4 hours at 50° C. After cooling overnight to room temperature, 13.5 ml of concentrated hydrochloric acid is added, and the mixture is poured into 7 l of methylene chloride. After one hour of agitation, the precipitate is vacuum-filtered and washed repeatedly with methylene chloride. After dissolving in 750 ml of water, the mixture is preliminarily distilled, and the aqueous solution is treated with a cation exchange resin and with an anion exchange resin. Then the filtered, neutral, aqueous solution is concentrated under vacuum, filtered over active carbon, and evaporated to dryness under vacuum, thus obtaining 86 g (70% of theory) of 5-cyano-2,4,6-triiodoisophthalic acid bis(2,3-dihydroxypropyl-N-methyl)diamide as a white powder with a decomposition point of above 280° C.

Analogously the following compounds are obtained:

5-cyano-2,4,6-triiodoisophthalic acid bis[bis(2-hydroxyethyl)]diamide, mp 212–215° C.; yield 78% of theory;

5-cyano-2,4,6-triiodoisophthalic acid bis[tris(hydroxymethyl)methyl]diamide, mp above 280° C.; yield 70% of theory;

5-cyano-3-(2,3-dihydroxypropylcarbamoyl)-2,4,6-triiodobenzoyl chloride, mp 285–288° C.; yield 60% of theory;

5-cyano-2,4,6-triiodoisophthalic acid bis(2,3-dihydroxypropyl)-diamide, mp above 280° C.; yield 80% of theory;

5-cyano-2,4,6-triiodoisophthalic acid mono-(2,3-dihydroxy-propyl)mono-(2,3-dihydroxypropyl-N-methyl)diamide, mp 215° C.; yield 81% of theory.

As indicated above primary or secondary amide groups can be N-alkylated in a conventional procedure. It is frequently advantageous (for example to avoid an otherwise necessary intermediate protection of hydroxy groups present in the molecule) to start with NR$_1$-substituted initial or starting compounds. Also in these cases, the introduction of the alkyl residue R$_1$ takes place according to methods known per se, as will be explained once more in detail, using as an example the preparation of 5-N,N-dimethylcarbamoyl-2,4,6-triiodoisophthalic acid from the corresponding 5-carbamoyl compound:

200 g of 5-carbamoyl-2,4,6-triiodoisphthalic acid is dissolved in 830 ml of 8N sodium hydroxide solution. Then a solution of 400 ml of dimethyl sulfate in 400 ml of acetone is added and the mixture heated for 6 hours to 60° C. After cooling overnight to room temperature, 1 l of ethyl acetate is added; the mixture is acidified with dilute hydrochloric acid, the ethyl acetate phase is separated, and the hydrochloric acid phase is extracted once more with 200 ml of ethyl acetate. The ethyl acetate phases are combined, dried over sodium sulfate, and then concentrated to dryness under vacuum. The residue is heated under reflux for 30 minutes with 750 ml of acetone. After several hours of agitation in an ice bath, the thus-separated crystalline product is vacuum-filtered, washed with a small amount of ice-cold acetone, and dried at 60° C., thus obtaining 188 g (90% of theory) of 5-N,N-dimethylcarbamoyl-2,4,6-triiodoisophthalic acid as a white powder having a decomposition point of above 280° C.

To prepare compounds of this invention according to Formula I with X meaning —$CH_2OH$, it is advantageous to start with initial or preliminary compounds wherein the residue —$CH_2OH$ is already included. Advantageously, for example, the starting compound is the conventional 5-amino-3-hydroxymethyl-2,4,6-triiodobenzoic acid, and the amino group is substituted by the cyano group, as described hereinabove and as will be once more explained in detail in the following example:

171 g of 5-amino-3-hydroxymethyl-2,4,6-triiodobenzoic acid is suspended in 3 l of water and dissolved by adding dilute sodium hydroxide solution. Then a pH of 2.5 is set by the addition of semiconcentrated sulfuric acid, and under cooling a solution of 28 g of sodium nitrite in 96 ml of water is added dropwise within 20 minutes in such a way that the reaction temperature ranges between 0° and +5° C. Thereafter the pH value is again set at 2.5 with semiconcentrated sulfuric acid, and the mixture is stirred for 2 hours in an ice bath. Subsequently the reaction mixture is neutralized under cooling with dilute sodium hydroxide solution, and poured into a solution of 143 g of copper(I) cyanide and 267 g of potassium cyanide in 1.3 l of water, during which step strong frothing occurs. The mixture is agitated for 30 minutes at room temperature, brought to pH 2.8 by adding concentrated hydrochloric acid, the precipitated copper salts are vacuum-filtered, the filtrate is brought to pH 0.5 by further addition of hydrochloric acid, and the mixture is agitated for several hours in an ice bath. The thus-formed precipitate is vacuum-filtered and, after washing with water, suspended in 3 l of water, extensively dissolved by adding concentrated ammonia, active carbon is added, and the mixture is allowed to stand under agitation at room temperature for 30 minutes. The mixture is vacuum-filtered, the filtrate is combined with excess concentrated hydrochloric acid, allowed to stand under agitation in an ice bath for several hours, and the precipitate is vacuum-filtered and dissolved in water-moist form in 1.3 l of acetone. After several hours of agitation in an ice bath, the crystallized product is vacuum-filtered, washed with ice-cold acetone, and dried at 50° C., thus obtaining 141 g (=81% of theory) of 5-cyano-3-hydroxymethyl-2,4,6-triiodobenzoic acid as a white powder, mp 250-252° C. (decomposition).

From this is obtained 5-hydroxymethyl-2,4,6-triiodoisophthalic acid in the above-described procedure, for example by saponifying the CN-group to —$CONH_2$ and diazotization of the latter to the COOH-group; this product can then be further processed according to process version (c) to esters or, in the form of the di-acid chloride according to, process version (a) to amides.

The same holds true for the preparation of compounds of Formula I with X meaning —$CH_2NHR_7$. Here again, initial or starting compounds are advantageously employed wherein the $CH_2NHR_7$ residue is predetermined. This will be explained in greater detail, using as an example 5-cyano-3-acetylaminomethyl-2,4,6-triiodobenzoic acid:

14 g of sodium nitrite is introduced under stirring into 170 ml of a concentrated sulfuric acid held at +5° C. The mixture is then maintained at +70° C. until solution has occurred, and then cooled to +5° C. After adding dropwise 84 ml of glacial acetic acid under cooling, 93.6 g of 5-amino-3-acetylaminomethyl-2,4,6-triiodobenzoic acid is added in incremental portions, maintaining the reaction temperature between 0° C. and +5° C. The reaction mixture is stirred for another 2 hours, poured on 800 g of ice, and, under cooling, introduced into a solution of 71 g of copper(I) cyanide and 133 g of potassium cyanide in a mixture of 1 l of concentrated ammonia and 640 ml of water. After several hours of stirring in an ice bath, the precipitated ammonium salt is vacuum-filtered and dissolved in 4 l of water. After filtration over active carbon, the filtrate is adjusted to pH 6 with acetic acid, again extracted with active carbon, filtered, and the filtrate combined with excess concentrated hydrochloric acid. The thus-separated precipitate is dried at 50° C., thus obtaining 80.5 g (=85% theory) of 5-cyano-3-acetylaminomethyl-2,4,6-triiodobenzoic acid as a white powder, mp 271° C. (decomposition).

If this initial product is to be further processed into a starting compound of Formula II, the cyano group is, for example, first saponified to the amide group —$CONH_2$, as described above, and this group is converted into the carboxy group with the aid of a diazotizing agent (preferably with $NaNO_2$ in an aqueous-acidic solution). The thus-obtained 2,4,6-triiodoisophthalic acid substituted in the 5-position by $CH_2NHR_7$-, for example 5-acetylaminomethyl-2,4,6-triiodoisophthalic acid, is then further processed into the finally desired compound of this invention according to Formula I by following process version (c) or, in the form of, for example, its di-acid chloride, according to process version (a).

If final products of general Formula I are to be prepared wherein Z means the residue —$NHR_7$, then it is suitable in certain cases to introduce the 5-positioned substituent —$CONHR_7$ already in an early preliminary stage. Preferably suitable are precursors with a 5-positioned cyano group, to the CN-triple bond of which the finally desired aliphatic carboxylic acid $R_7COOH$ is chemically added in a manner known per se—as explained above in describing process version (b). The $R_7COOH$-addition will be explained once more in detail, using as example 5-cyano-1,4,6-triiodoisphthalic acid monodimethylamide:

6 g of 5-cyano-2,4,6-triiodoisophthalic acid monodimethylamide is suspended in 30 ml of acetic anhydride. After adding 0.5 ml of 80% perchloric acid, the reaction mixture is held for 3 hours at 90-95° C., filtered over active carbon, added dropwise under cooling in 200 ml of water, and dissolved by adding sodium carbonate at pH 10. After treatment with active carbon, the solution is combined with excess concentrated hydrochloric acid, and the thus-obtained precipitate is dissolved, after vacuum-filtering and washing with water, in 40 ml of acetone. After several hours of agitation in an ice bath, the crystallized product is vacuum-filtered, washed with a small amount of ice-cold acetone, and dried at 50° C., thus obtaining 4.5 g of 5-acetylamino-carbonyl-2,4,6-triiodoisophthalic acid monodimethylamide as a white powder having a decomposition point above 280° C.

Analogously, the following compound is obtained from the corresponding 5-cyano compound: 5-acetylaminocarbonyl-2,4,6-triiodoisophthalic acid, mp 185° C. (decomposition); yield 80% of theory.

If it becomes necessary during the course of the process for producing the compounds of Formula I according to the invention to saponify an intermediately formed acid halogenide group, e.g. an acid chloride group, to the free carboxy group, this saponification reaction likewise takes place according to generally customary methods, as will be explained in detail, using as example 5-chloroformyl-2,4,6-triiodoisophthalic acid [(2,3-dihydroxypropyl)-(N,N-dimethyl)]diamide:

7 g of 5-chloroformyl-2,4,6-triiodoisophthalic acid [(2,3-dihydroxypropyl)-(N,N-dimethyl)]diamide is dissolved in 15 ml of dimethyl sulfoxide. After the addition of 5 ml of 2N sodium hydroxide solution, the mixture is allowed to stand overnight at room temperature and then concentrated to dryness under vacuum. The residue is taken up in 20 ml of water, filtered over active carbon, and combined under agitation with excess concentrated hydrochloric acid. After several hours of stirring, the thus-formed precipitate is vacuum-filtered, washed with a small amount of ice-cold water, and dried at 50° C., thus obtaining 6.2 g (=90% of theory) of 5-N,N-dimethylcarbamoyl-2,4,6-triiodoisophthalic acid mono-2,3-dihydroxypropylamide as a white powder, mp 255–258° C. (decomposition).

As described above, the esterification of free carboxy groups takes place according to known methods, wherein methods disclosed for the esterification of triiodinated aminobenzoic acid derivatives are preferred and as will be described once more by the following example:

60 g 5-cyano-2,4,6-triiodoisophthalic acid monomethylamide is heated in 150 ml of dimethylformamide with 22 g of sodium carbonate (anhydrous) and 28 g of 1-chloro-2,3-propanediol for 4 hours to 90° C. The mixture is then cooled, vacuum-filtered from the precipitated sodium chloride, and concentrated to dryness under vacuum. The residue is dissolved in 250 ml of ethyl acetate, the solution is filtered over active carbon, and the filtrate is concentrated to half its volume. The product is cooled in an ice bath and gently combined with such an amount of diisopropyl ether that crystallization sets in. After stirring for several, hours in an ice bath, the crystallized product is vacuum-filtered, washed with diisopropyl ether, and dried at 50° C., thus obtaining 48.5 g (=74% of theory) of 5-cyano-3-methylcarbamoyl-2,4,6-triiodobenzoic acid (2,3-dihydroxypropyl)ester as a white powder, mp 117–120° C.

Starting compounds according to this process can also be prepared from 3,5-diamino-2,4,6-triiodobenzoic acid by substituting analogously as described above the 3- and 5-positioned amino group by the cyano group and then saponifying the latter to the carbamoyl group. The thus-obtained 3,5-bis-carbamoyl-2,4,6-triiodobenzoic acid is then diazotized as disclosed above to the 2,4,6-triiodotrimesic acid.

7 g of sodium nitrite is introduced under stirring into 84 ml of a concentrated sulfuric acid held at a temperature of +5° C. The mixture is then maintained at +70° C. until solution has occurred, and then cooled to +5° C. After adding dropwise 42 ml of glacial acetic acid under thorough cooling, 21 g of 3,5-diamino-2,4,6-triiodobenzoic acid (purified by way of the dioxane adduct) is added under agitation in incremental portions so that the internal temperature ranges between 0° C. and +5° C. The batch is stirred for another 2 hours and the green-colored suspension is poured on 400 g of ice. A mixture is prepared from 500 ml of concentrated ammonia and 320 ml of water, and 35.6 g of copper(I) cyanide and 67 g of potassium cyanide are dissolved therein. The diazotizing batch is added to this solution, during which step strong frothing occurs. The mixture is stirred for another 2 hours,, and the charge is then combined, after standing overnight, first with 500 ml of ethyl acetate, then with excess concentrated hydrochloric acid. After vacuum-filtering the separated copper salts, which are washed out with ethyl acetate, the aqueous phase in the filtrate is separated and several times extracted with ethyl acetate. The ethyl acetate extracts are combined, washed with water, and then dried over sodium sulfate and concentrated. The dark-colored residue is treated under heating with 100 ml of acetone; the acetone solution is filtered off from undissolved components, and then concentrated to half its volume. After several hours of agitation, the crystallized product is vacuum-filtered, washed with ice-cold acetone, and dried at 50° C., thus obtaining 8.5 g (=38% of theory) of 3,5-dicyano-2,4,6-triiodobenzoic acid as a white powder having a decomposition point above 280° C.

10 g of 3,5-dicyano-2,4,6-triiodobenzoic acid is suspended in 100 ml of water and dissolved by adding 2 g of sodium hydroxide. The reaction mixture is held at +60° C. for 3 hours. Subsequently the thus-obtained 3,5-biscarbamoyl-2,4,6-triiodibenzoic acid solution is combined with 100 ml of concentrated hydrochloric acid and heated to 90° C. Under continuous agitation, a solution of 12 g of sodium nitrite in 60 ml of water is introduced within 5 hours underneath the level of the solution. The mixture is agitated for another 2 hours at 90° C., then concentrated to dryness under vacuum, and the residue extracted with 100 ml of diisopropyl ether. The product is vacuum-filtered from the precipitated sodium chloride and the filtrate concentrated to dryness, thus obtaining 10 g of 2,4,6-triiodobenzene-1,3,5-tricarboxylic acid as a white powder having a decomposition point lying above 280° C. Yield: 93% of theory.

Optionally, the 3,5-biscarbamoyl-2,4,6-triiodobenzoic acid can be isolated in the usual way from the above-obtained 3,5-biscarbamoyl-2,4,6-triiodobenzoic acid sodium salt solution, mp above 300° C.; yield: 90%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2,4,6-Triiodobenzene-1,3,5-tricarboxylic Acid Tris(2,3-dihydroxy/propyl-N-methyl)triamide 127.1 g of triiodotrimesic acid trichloride is dissolved in 254 ml of dimethylacetamide at 50° C. Then a solution of 145.2 g of N-methylamino-2,3-propanediol is added dropwise under agitation within 15 minutes so that an internal temperature of 60° C. is not exceeded. Subsequently, the reaction mixture is stirred for 4 hours at 50° C. After standing overnight, 20 ml of concentrated hydrochloric acid is added and the mixture concentrated to dryness under vacuum. The residue is dissolved in 1 l of water and treated first with 1.5 l of a cation exchange resin and then the filtrate is treated with 15 l of an anion exchange resin. The colorless, salt-free filtrate is then concentrated under vacuum to dryness and the residue dried at 50° C., mp 150–152° C.; yield: 134 g (80% of theory).

EXAMPLE 2

2,4,6-Triiodobenzene-1,3,5-tricarboxylic Acid Tris(2,3,4,5,6-pentahydroxyhexyl-N-methyl)triamide 68.3 g of N-methylglucamine is suspended in 175 ml of dimethylacetamide; the suspension is then heated to 50° C. Then, under agitation at 50° C., a solution of 32.2 g of triiodotrimesic acid trichloride in 75 ml of dimethylacetamide is added dropwise within 15 minutes. Thereafter the reaction mixture is stirred for another 4 hours at 50° C. After standing overnight, 6 ml of concentrated hydrochloric acid is added, and the mixture is stirred for 30 minutes. The separated N-methylglucamine hydrochloride is vacuum-filtered and discarded after washing with a small amount of dimethylacetamide. The filtrate is concentrated under vacuum and the remaining crude product is purified analogously to Example 1 by way of exchange resins, mp 112–119° C.; yield: 34.3 g (61% of theory).

EXAMPLE 3

2,4,6-Triiodobenzene-1,3,5-tricarboxylic Acid Tris[bis(2-hydroxyethyl)]triamide 113 g of triiodotrimesic acid trichloride is dissolved in 226 ml of dimethylacetamide at 50° C. Then a solution of 73.9 g of diethanolamine in 148 ml of dimethylacetamide is added dropwise within 25 minutes so that an internal temperature of 60° C. is not exceeded. Subsequently the reaction mixture is stirred for 4 hours a 50° C. After standing overnight, 30 ml of hydrochloric acid is added and the solution is introduced dropwise under agitation into 2.8 1 of methylene chloride. The mixture is stirred for another hour, the supernatant methylene chloride is decanted off, and the residue is extracted once more with 1 1 of methylene chloride. The separated residue is dried under vacuum at 50° C., then dissolved in 1 1 of water, and the solution purified analogously to Example 1 by treatment with exchange resins. The desired product is isolated by concentration of the aqueous solution under vacuum, mp 132–135° C.; yield: 72.3 g (49% of theory).

EXAMPLE 4

2,4,6-Triiodobenzene-1,3,5-tricarboxylic Acid Tris[1,1-bis(hydroxymethyl)methyl]triamide This compound is obtained analogously to Example 3 with 2-amino-1,3-propanediol, mp >300° C.; yield: 68% of theory.

EXAMPLE 5

2,4,6-Triiodobenzene-1,3,5-tricarboxylic Acid Tris(2,3-dihydroxypropyl)triamide

This compound is produced analogously to Example 3 with 1-amino-2,3-propanediol, mp >300° C.; yield: 70% of theory.

EXAMPLE 6

(-)2,4,6-Triiodobenzene-1,3,5-tricarboxylic Acid Tris[(R)-2,3-dihydroxypropyl]triamide This compound is obtained as the base analogously to Example 3 with (+)(R)-1-amino-2,3-propanediol, mp >300° C.; $[\alpha]_D^{20} = -3.5°$; yield: 66% of theory.

EXAMPLE 7

2,4,6-Triiodobenzene-1,3,5-tricarboxylic Acid Tris(2-hydroxyethyl)triamide 12.9 g of 2,4,6-triiodotrimesic acid trichloride is dissolved in 26 ml of dimethylacetamide. Then a solution of 8.4 ml of ethanolamine in 20 ml of dimethylacetamide is added dropwise within 10 minutes so that an internal temperature of 60° C. is not exceeded Subsequently the reaction mixture is stirred for 4 hours at 50° C. After standing overnight, 2 ml of concentrated hydrochloric acid is added to the solution and the latter is concentrated under vacuum. The residue is stirred with 20 ml of water, vacuum-filtered, and dried at 50° C., mp >300° C.; yield: 13.0 g (91% of theory).

EXAMPLE 8

2,4,6-Triiodobenzene-1,3,5-tricarboxylic Acid Tris(2-hydroxyethyl-N-methyl)triamide This compound is obtained analogously to Example 7 with N-methylethanolamine as the base, mp 284–285° C.; yield: 60% of theory.

EXAMPLE 9

2,4,6-Triiodobenzene-1,3,5-tricarboxylic Acid Tris(b 2-hydroxypropyl)triamide

This compound is produced analogously to Example 7 with 1-amino-2-propanol as the base, mp 294–295° C.; yield: 65% of theory.

EXAMPLE 10

5-Carbamoyl-2,4,6-triiodoisophthalic Acid Bis(2,3-dihydroxypropyl-N-methyl)diamide 200 g of 5-cyano-2,4,6-triiodoisophthalic acid bis-(2,3-dihydroxypropyl-N-methyl)diamide is dissolved in 540 ml of water and 69.5 ml of concentrated sodium hydroxide solution and stirred for 3 hours at 60° C. The solution is combined analogously to Example 3 with concentrated hydrochloric acid, the solution is purified by way of ion exchangers, and the product is obtained by concentrating the salt-free aqueous solution under vacuum at 50° C., mp 192–194° C.; yield: 147 g (72% of theory).

EXAMPLE 11

5-Carbamoyl-2,4,6-triiodoisophthalic Acid N,N,N',N'-tetrakis(2-hydroxyethyl)diamide This compound is obtained analogously to Example 10 by partial saponification of 5-cyano-2,4,6-triiodoisophthalic acid N,N,N',N'-tetrakis(2-hydroxyethyl)diamide, mp 198–200° C.; yield: 69% of theory.

EXAMPLE 12

5-Carbamoyl-2,4,6-triiodoisophthalic Acid Bis[tris(hydroxymethyl)methyl]diamide

This compound is obtained analogously to Example 10 by partial saponification of 5-cyano-2,4,6-triiodoisophthalic acid bis[tris(hydroxymethyl)methyl]diamide, mp > 300° C.; yield: 67% of theory.

EXAMPLE 13

5-Carbamoyl-2,4,6-triiodoisophthalic Acid Bis(2,3-dihydroxypropyl)diamide 95 g of 5-cyano-2,4,6-triiodoisophthalic acid bis(2,3-dihydroxypropyl)diamide is introduced under agitation in incremental portions into a solution of 20 g of sodium hydroxide in 500 ml of water. The mixture is agitated for 4 hours at room temperature. The clear solution is brought to pH 7 with concentrated hydrochloric acid, filtered over active carbon, and concentrated under vacuum. The residue is extracted under boiling with 500 ml of a mixture of equal parts of methanol and ethanol for 30 minutes. The sodium chloride is filtered off and the filtrate concentrated to dryness under vacuum. The residue is dried under vacuum at 50° C., mp > 300° C.; yield: 80 g (73% of theory).

EXAMPLE 14

5-Carbamoyl-2,4,6-triiodoisophthalic Acid Bis[1,1-bis(hydroxymethyl)methyl]diamide 11 g of 5-carbamoyl-2,4,6-triiodoisophthalic acid dichloride is dissolved in 22 ml of dimethylacetamide. Then a solution of 40 g of 2-amino-1,3-propanediol in 15 ml of dimethylacetamide is added dropwise under agitation within 10 minutes in such a way that an internal temperature of 60° C. is not exceeded. Subsequently the reaction mixture is stirred for 4 hours at 50° C. After standing overnight, 2.4 ml of concentrated hydrochloric acid is added and the solution is added dropwise under stirring to 270 ml of methylene chloride. After one hour, the supernatant methylene chloride is removed by decanting and the residue is again extracted with 200 ml of methylene chloride. The separated residue is dried under vacuum at 50° C., then dissolved in 100 ml of water, and the solution, filtered over active carbon, is purified with ionexchange resins analogously to Example 1. The desired product is isolated by concentration of the aqueous solution under vacuum, mp 248–252° C.; yield: 8.4 g (65% of theory).

EXAMPLE 15

5-N-Methylcarbamoyl-2,4,6-triiodoisophthalic Acid Bis(2,3-dihydroxypropyl-N-methyl)diamide 62.3 g of 5-N-methylcarbamoyl-2,4,6-triiodoisophthalic acid dichloride is stirred with 125 ml of dimethylacetamide heated to 50° C. Under agitation, a solution of 30.8 of N-methylamino-2,3-propanediol in 62 ml of dimethylacetamide is added dropwise to this reaction mixture. Then, 69.6 ml of tri-n-butylamine is added thereto. Subsequently the reaction mixture is stirred for 4 hours at 50° C. After standing overnight, 18 ml of concentrated hydrochloric acid is added and the solution is stirred into 3 l of methylene chloride. The mixture is agitated for another hour, the supernatant methylene chloride is removed by decanting, and the residue is again extracted with 500 ml of methylene chloride. The separated residue is dried under vacuum at 50° C., then dissolved in 500 ml of water, and the solution, filtered over active carbon, is purified with ion-exchange resins analogously to Example 1. The desired product is isolated by concentration of the aqueous solution under vacuum, mp 178–182° C.; yield: 57.6 g (76% of theory).

EXAMPLE 16

5-N-Methylcarbamoyl-2,4,6-triiodoisophthalic Acid N,N,N',N'-tetrakis(2-hydroxyethyl)diamide This compound is obtained analogously to Example 15 with diethanolamine as the base, mp 167–174° C.; yield: 55% of theory.

EXAMPLE 17

5-N,N-Dimethylcarbamoyl-2,4,6-triiodoisophthalic Acid Bis(2,3-dihydroxypropyl)diamide 60 g of 5-N,N-dimethylcarbamoyl-2,4,6-triiodoisophthalic acid dichloride is dissolved in 76 ml of dimethylacetamide at 50° C. Then a solution of 13.9 g of 1-amino-2,3-propanediol in 46 ml of dimethylacetamide is added dropwise under agitation within 10 minutes so that an internal temperature of 60° C. is not exceeded. Subsequently the reaction mixture is stirred for 4 hours at 50° C. After standing overnight, 5 ml of concentrated hydrochloric acid is added, and the solution is added dropwise under agitation to 2 l of methylene chloride. The mixture is agitated for another hour, the methylene chloride is removed by decanting, the residue is extracted once more with 500 ml of methylene chloride, and then dried, after separation of the methylene chloride, at 50° C. under vacuum. The product is dissolved in 500 ml of water and the solution is purified analogously to Example 1 by treatment with ion-exchange resins. The desired product is isolated by concentration of the aqueous solution under vacuum, mp 200–201° C.; yield: 34 g (73% of theory).

EXAMPLE 18

(-)5-N,N-Dimethylcarbamoyl-2,4,6-triiodoisophthalic Acid Bis(2,3-dihydroxypropyl)diamide This compound is obtained analogously to Example 17 with (+) (R)-1-amino-2,3-propanediol, mp 199–200° C.; $[\alpha]_D^{20} = -2.2°$; yield: 68% of theory.

EXAMPLE 19

5-N,N-Dimethylcarbamoyl-2,4,6-triiodoisophthalic Acid Bis(2,3-dihydroxypropyl-N-methyl)diamide This compound is produced analogously to Example 17 with N-methylamino-2,3-propanediol as the base, mp 185–187° C.; yield: 69% of theory.

EXAMPLE 20

5-N,-N-Dimethylcarbamoyl-2,4,6-triiodoisophthalic Acid Bis[bis(hydroxymethyl)methyl]diamide This compound is obtained analogously to Example 17 with 2-amino-1,3-propanediol as the base, mp > 300° C.; yield: 72% of theory.

EXAMPLE 21

5-N,N-Dimethylcarbamoyl-2,4,6-triiodoisophthalic Acid N,N,N',N'-tetrakis(2-hydroxyethyl)diamide This compound is prepared in analogy to Example 17 with diethanolamine as the base, mp 158–160° C.; yield: 70% of theory.

EXAMPLE 22

5-N,N-Dimethylcarbamoyl-2,4,6-triiodoisophthalic Acid Bis[Tris(hydroxymethyl)methyl]diamide This compound is obtained analogously to Example 17 with 2-amino-2-(hydroxymethyl)-1,3-propanediol as the base, mp > 300° C.; yield: 67% of theory.

EXAMPLE 23

5-N,N-Dimethylcarbamoyl-2,4,6-triiodoisophthalic Acid (2,3-Dihydroxypropyl)-(2,3-dihydroxypropyl-N-methyl)diamide 5 l of dioxane is heated to 80° C. and combined in succession with 50 g of 1-amino-2,3-propanediol and 145 g of 5-N,N-dimethylcarbamoyl-2,4,6-triiodoisophthalic acid dichloride. After 10 minutes of agitation at 80° C., the mixture is quickly cooled, filtered over kieselguhr, and concentrated to dryness under vacuum. The residue is extracted by boiling repeatedly with respectively 500 ml of ethyl acetate, then vacuum-filtered, and dried at 60° C., thus obtaining 69.2 g (45% of theory) of 5-chloroformyl-2,4,6-triiodoisophthalic acid (2,3-dihydroxypropyl)-(N,N-dimethyl)diamide as a white powder, mp 145–147° C. (decomposition).

50 g of the acid chloride is introduced in incremental portions under stirring and cooling into a solution of 15.9 g of N-methylamino-2,3-propanediol in 144 ml of dimethyl acetamide so that the reaction temperature does not rise above 40° C. After agitating overnight, the solution is concentrated under vacuum, the oily residue is dissolved in 50 ml of water the solution is brought to pH 7 by adding concentrated hydrochloric acid and purified analogously to Example 1 over exchange resins. The thus-purified product is isolated by concentration of the aqueous solution and dried at 50° C., mp 105–107° C.; yield: 12 g (68% of theory).

EXAMPLE 24

5-Carbamoyl-2,4,6-triiodoisophthalic Acid (2,3-Dihydroxypropyl)-(2,3-dihydroxypropyl-N-methyl)diamide This compound is obtained analogously to Example 10 by partial saponification of 5-cyano-2,4,6-triiodoisophthalic acid (2,3-dihydroxypropyl)-(2,3-dihydroxypropyl-N-methyl)diamide, mp 200–202° C.; yield: 70% of theory.

EXAMPLE 25

5-N,N-Dimethylcarbamoyl-2,4,6-triiodoisophthalic Acid Bis(2,3-dihydroxypropyl)diester 12.2 g of 5-N,N-dimethylcarbamoyl-2,4,6-triiodoisophthalic acid is suspended in 100 ml of water and dissolved by adding concentrated sodium hydroxide solution at pH 7. The mixture is then concentrated to dryness under vacuum and the anhydrous disodium salt is dissolved in 30 ml of dimethylformamide. After the addition of 11 g of 1-chloro-2,3-propanediol, the reaction mixture is heated for 4 hours to 90° C. After cooling to room temperature, the sodium chloride is separated and the solution is concentrated under vacuum. The residue is extracted by boiling with 120 ml of acetone and the solution filtered in the hot state over active carbon. Then 1 ml of concentrated hydrochloric acid is added, and the solution is concentrated to 50 ml. After cooling to 5° C., such an amount of diisopropyl ether is added that crystallization occurs. After several hours of agitation in an ice bath, the crystallized product is vacuum-filtered, washed with diisopropyl ether, and dried at 50° C., mp 145° C.; yield: 9.4 g (62% of theory).

EXAMPLE 26

5-N-Methylcarbamoyl-2,4,6-triiodoisophthalic Acid Bis(2,3-dihydroxy-l-hydroxymethylpropyl)diamide This compound is obtained analogously to Example 15 with 2-amino-1,3,4-trihydroxybutane as the base, mp starting with 185° C.; yield: 58.3% of theory.

| Example for Form of Administration: | |
|---|---|
| 5-Carbamoyl-2,4,6-triiodoisphthalic acid bis(2,3-dihydroxypropyl-N-methyl)diamide | 599.74 g |
| Calcium disodium salt of ethylenediaminetetraacetic acid | 0.10 g |
| Sodium bicarbonate | 1.23 g |
| Aqua bidestillata to a volume of | 1000 ml |

Procedure: 5-Carbamoyl-2,4,6-triiodoisophthalic acid bis(2,3-dihydroxypropyl-N-methyl)diamide is dissolved, after adding calcium disodium salt of ethylenediaminetetraacetic acid, in aqua bidestillata. The pH is brought to 7 by adding sodium bicarbonate, the volume is replenished to 1000 m by the addition of aqua bidestillata, and the thus-obtained solution is then heat-sterilized. Iodine content: 300 mg/ml.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 2,4,6-Triiodobenzene-1,3,5-tricarboxylic acid tris(2,3-dihydroxypropyl-N-methylamide).

2. 2,4,6-Triiodobenzene-1,3,5-tricarboxylic acid tris[bis(2-hydroxyethyl)]triamide.

3. 5-N-Methylcarbamoyl-2,4,6-triiodiosophthalic acid bis(2,3-dihydroxy-1-hydroxymethylpropyl)diamide.

4. An X-ray contrast medium comprising an amount of a compound of claim 1 effective to make the medium opaque to X-rays after it has been administered to a host undergoing X-ray diagnosis, and a pharmaceutically acceptable carrier.

5. The X-ray contrast medium of claim 4 wherein the amount of opaque agent is 50–400 mg I/ml of medium.

6. A method of rendering an inner cavity of a host opaque to X-rays, comprising administering an X-ray contrast medium of claim 4 to the host in such a manner that it passes through the inner cavity and in such an amount that, when the medium reaches the inner cavity, it renders the cavity opaque to X-rays.

7. A method of conducting angiography, urography, lymphography, computer tomography, bronchography, gastrointestinal visualization, arthrography or myelography on a patient in need of the same which comprises first administering an X-ray contrast medium in accordance with claim 6 and then exposing the patient to diagnostic X-raying.

8. An X-ray contrast medium comprising an amount of a compound of claim 2 effective to make the medium opaque to X-rays after its has been administered to a host undergoing X-ray diagnosis, and a pharmaceutically acceptable carrier.

9. The X-ray contrast medium of claim 8, wherein the amount of opaque agent is 50–400 mg I/ml of medium.

10. A method of rendering an inner cavity of a host opaque to X-rays, comprising administering an X-ray contrast medium of claim 8 to the host in such a manner that it passes through the inner cavity and in such an amount that, when the medium reaches the inner cavity, it renders the cavity opaque to X-rays.

11. A method of conducting angiography, urography, lymphography, computer tomography, bronchography, gastrointestinal visualization, arthrography or myelography on a patient in need of the same which comprises first administering an X-ray contrast medium in accordance with claim 10 and then exposing the patient to diagnostic X-raying.

12. An X-ray contrast medium comprising an amount of a compound of claim 13 effective to make the medium opaque to X-rays after it has been administered to a host undergoing X-ray diagnosis, and a pharmaceutically acceptable carrier.

13. The X-ray contrast medium of claim 12, wherein the amount of opaque agent is 50–400 mg I/ml of medium.

14. A method of rendering an inner cavity of a host opaque to X-rays, comprising administering an X-ray contrast medium of claim 12 to the host in such a manner that it passes through the inner cavity and in such an amount that, when the medium reaches the inner cavity, it renders the cavity opaque to X-rays.

15. A method of conducting angiography, urography lymphography, computer tomography, bronchography, gastrointestinal visualization, arthrography, or myelography on a patient in need of the same which comprises first administering an X-ray contrast medium in accordance with claim 14 and then exposing the patient to diagnostic X-raying.

* * * * *

UNITED STATES PATENT AND TRADEMARK OFFICE
CERTIFICATE OF CORRECTION

PATENT NO. : 5,047,228

DATED : September 10, 1991

INVENTOR(S) : Gries et al.

It is certified that error appears in the above-identified patent and that said Letters Patent is hereby corrected as shown below:

Column 25:

Claim 12; Line 2: reads - - -

(of a compound of claim 13)

Should read - - -

" of a compound of claim 3 "

Signed and Sealed this

Second Day of March, 1993

*Attest:*

STEPHEN G. KUNIN

*Attesting Officer*     *Acting Commissioner of Patents and Trademarks*